United States Patent
Shalaby et al.

(10) Patent No.: US 7,465,489 B2
(45) Date of Patent: Dec. 16, 2008

(54) INORGANIC-ORGANIC MELTED-EXTRUDED HYBRID FILAMENTS AND MEDICAL APPLICATIONS THEREOF

(75) Inventors: Shalaby W Shalaby, Anderson, SC (US); Kenneth W Clinkscales, Easley, SC (US); Kimberly A. Carpenter, Pendleton, SC (US)

(73) Assignee: Poly-Med, Inc., Anderson, SC (US)

( * ) Notice: Subject to any disclaimer, the term of this patent is extended or adjusted under 35 U.S.C. 154(b) by 80 days.

(21) Appl. No.: 11/599,691

(22) Filed: Nov. 15, 2006

(65) Prior Publication Data

US 2007/0110999 A1    May 17, 2007

Related U.S. Application Data

(60) Provisional application No. 60/737,022, filed on Nov. 15, 2005.

(51) Int. Cl.
*B32B 25/02* (2006.01)
*C04B 32/33* (2006.01)

(52) U.S. Cl. .................. 428/296.7; 264/638; 264/839; 264/640; 264/641

(58) Field of Classification Search .............. 428/296.7; 264/638–641
See application file for complete search history.

(56) References Cited

U.S. PATENT DOCUMENTS

| 4,529,368 | A * | 7/1985 | Makansi | 425/72.2 |
| 6,462,169 | B1 | 10/2002 | Shalaby | |
| 6,485,749 | B1 * | 11/2002 | Shalaby | 424/486 |
| 6,794,485 | B2 | 9/2004 | Shalaby et al. | |
| 6,986,859 | B2 * | 1/2006 | Mazany et al. | 264/234 |
| 2003/0105256 | A1 * | 6/2003 | Shalaby | 526/312 |
| 2005/0277349 | A1 * | 12/2005 | Smith et al. | 442/59 |

* cited by examiner

*Primary Examiner*—Lynda Salvatore
(74) *Attorney, Agent, or Firm*—Leigh P Gregory

(57) ABSTRACT

This invention deals with a family of inorganic-organic hybrid, melt-extruded filaments having variable cross-sectional geometry with a cross-sectional area ranging between 100 $\mu^2$ and 4 $mm^2$, wherein the inorganic component comprises at least 10 weight percent of the total system and is present as dispersed micro-/nanoparticles in an organic absorbable or non-absorbable matrix representing no more than 90 weight percent. Hybrid filaments are particularly useful for the production of absorbable/disintegratable coil components of an absorbable/disintegratable endoureteral stent and radiopaque surgical markers or sutures.

8 Claims, No Drawings

INORGANIC-ORGANIC MELTED-EXTRUDED HYBRID FILAMENTS AND MEDICAL APPLICATIONS THEREOF

CROSS-REFERENCE TO RELATED APPLICATIONS

This application claims the benefit of prior provisional application Ser. No. 60/737,022, filed Nov. 15, 2005.

FIELD OF THE INVENTION

This invention relates to a new family of inorganic-organic hybrid filaments employing specialized conditions for uniformly dispersing microparticles of the inorganic component into an organic absorbable or non-absorbable polymeric matrix at a weight concentration of at least about 10 percent to produce a hybrid microcomposite which can be extruded under specially designed conditions into filaments of variable cross-sectional geometries having a cross-sectional area ranging from about 100 $\mu^2$ to about 4 $mm^2$, to meet special medical and/or pharmaceutical requirements for unique, value-added products.

BACKGROUND OF THE INVENTION

Traditional melt-extruded, fine filaments of different cross-sectional geometries having a cross-sectional area at or below 4 $mm^2$ and particularly those having a cross-sectional area of less than 2 $mm^2$ such as monofilament and multifilament yams used for manufacturing different knitted and woven textile constructs, monofilament sutures, and multifilament braided sutures, are known to be based on thermoplastic crystalline polymers comprising linear chains. An exception to the traditional practice was disclosed by one of the inventors, wherein polyaxial polymers (with a monocentric branching point) were prepared and converted to strong monofilaments useful for the production of surgical sutures and allied medical products (U.S. Pat. Nos. 6,462,169 and 6,794,485). It is also traditional to incorporate less than 2 weight percent of solid inorganic additives in textile fibers as delustering agents (e.g., $TiO_2$) and to a lesser extent, colorants and heat stabilizers. And frequently, these additives tend to cluster in the polymer melt and interfere with extrusion of articles having small cross-sectional areas as in the case of fiber melt-spinning. In spite of the availability of a great number of inorganic additives that can conceptually impart unique and useful properties to extruded filaments, if used in quantities exceeding 2 weight percent, investigators of the prior art have failed to explore this option to avoid known or perceived complications in the melt-spinning of such inorganic-organic hybrid systems. These facts and contemporary needs for unique hybrid microcomposites in filament form provided a strong incentive to pursue the present invention, which is directed to a new family of inorganic-organic hybrid filaments containing at least 10 weight percent of at least one inorganic component uniformly dispersed as microparticles in an organic polymeric matrix to impart one or more useful properties to medical and/or pharmaceutical devices made thereof.

SUMMARY OF THE INVENTION

The present invention is directed to with an inorganic-organic hybrid melt-extruded filament comprising at least 10 weight percent of at least one type of inorganic micro-/nanoparticles dispersed in a thermoplastic organic polymeric matrix, wherein the inorganic micro-/nanoparticles are selected from the group represented by sulfates of multivalent metals, phosphate salts, polymeric phosphate glasses, polymeric phosphate glass ceramics, phosphate ceramics, $ZrO_2$, and basic bismuth carbonate. Specifically, the inorganic components are selected from sulfates of at least one metal selected from the group consisting of Mg, Ca, Ba, Sr, Zr, Zn, Bi, and Fe; phosphate salts such as at least one of those selected from the group represented by $CaHPO_4$, $K_2HPO_4$, $KH_2PO_4$, $Na_2HPO_4$, $NaH_2PO_4$, $Ca_3(PO_4)_2$, $Ca_{10}(OH)_2(PO_4)_6$, and $Ca_2P_2O_7$; and/or polymeric phosphate glasses which are derived from $P_2O_5$, CaO, and at least one oxide selected from the group represented by ZnO, SrO, $Na_2O$, $K_2O$, $SiO_2$, $Fe_2O_3$, and $ZrO_2$. Also, the organic polymeric matrix of the inorganic-organic hybrid melt-extruded filament may consist of (1) a thermoplastic absorbable polyester comprising chain sequences derived from one or more cyclic monomer selected from the group represented by ε-caprolactone, glycolide, a lactide, p-dioxanone, 1,5-dioxepan-2-one, trimethylene carbonate, and a morpholinedione; (2) an absorbable polyether-ester which may be derived from a polyethylene glycol end-grafted with at least one cyclic monomer selected from the group represented by ε-caprolactone, glycolide, a lactide, trimethylene carbonate, p-dioxanone, 1,5-dioxepan-2-one, and a morpholinedione; or (3) polypropylene.

A specific aspect of this invention deals with an inorganic-organic hybrid melt-extruded filament including at least 10 weight percent of at least one type of inorganic micro-/nanoparticles dispersed in a thermoplastic organic polymeric matrix, wherein the said filament is a monofilament having a diameter of less than about 2 mm which includes inorganic microparticles of $BaSO_4$ dispersed in an organic polymer, specifically an absorbable polyester having chain sequences derived from at least one cyclic monomer selected from the group represented by ε-caprolactone, glycolide, a lactide, p-dioxanone, 1,5-dioxepan-2-one, trimethylene carbonate, and a morpholinedione, wherein the monofilament is heat-set into a coil for use as a component of an endoureteral stent.

Another specific aspect of this invention deals with an inorganic-organic hybrid melt-extruded filament including at least 10 weight percent of at least one type of inorganic micro-/nanoparticles dispersed in a thermoplastic organic polymeric matrix, wherein the said filament is a monofilament having a diameter of less than about 2 mm, wherein the inorganic micro-/nanoparticles are formed of $BaSO_4$ and the organic polymer is an absorbable polyether-ester. Preferably, the absorbable polyether-ester is derived from a polyethylene glycol grafted with at least one cyclic monomer selected from the group represented by ε-caprolactone, glycolide, a lactide, p-dioxane, 1,5-dioxepan-2-one, trimethylene carbonate and a morpholinedione. The monofilaments formed of the absorbable polyesters or the polyether-esters described above as the organic matrix can be used as a component of an endourological stent, wherein the endourological stent is an endoureteral device formed from the hybrid monofilament as a coil covered with a knitted absorbable mesh and a binder surface coating; or a radiopaque component of a medical device. Another specific aspect deals with an inorganic-organic hybrid melt-extruded filament comprising at least 10 weight percent of at least one type of inorganic micro-/nanoparticles dispersed in a thermoplastic organic polymeric matrix, wherein the aid filament can be used (1) as a radiopaque surgical device selected from the group represented by absorbable suture, absorbable stent, non-absorbable retraction tape, and non-absorbable suture; and/or (2) for cancer-related surgeries.

Other specific aspects of this invention deal with (1) an inorganic-organic hybrid melt-extruded filament comprising at least 10 weight percent of at least one type of inorganic micro-/nanoparticles dispersed in a thermoplastic organic polymeric matrix, wherein the filament is formed using melt extrusion; (2) a process for in situ formation of the hybrid composition used in the melt-extrusion of the filament; and (3) a process for converting the hybrid composition to the filament.

DETAILED DESCRIPTION OF PREFERRED EMBODIMENTS

It is commonly believed that incorporation of more than 5 and even 2 weight percent of inorganic additives needed to impart useful properties to extruded filaments of crystalline polymers will impair their extrusion into filaments having small cross-sectional areas such as those ranging between 100 $\mu^2$ and 4 $mm^2$. Contrary to this belief, the present invention is directed to hybrid inorganic-organic compositions comprising at least 10 weight percent of an inorganic component present as uniformly dispersed micro-/nanoparticles in an absorbable or non-absorbable organic polymeric matrix, which are converted under controlled extrusion conditions to filaments having wide ranges of cross-sectional areas and geometries. These filaments can be produced as (1) monofilament yarn with circular or elliptical cross-sectional area for use, subsequently, in manufacturing surgical sutures, radiomarkers, components of composite surgical meshes, and/or components or load-bearing springs (or coils) of endourological devices, particularly endoureteral devices (as described in copending U.S. patent application Ser. No. 11/204,822) and endovascular devices; (2) multifilament yarns for use as components of knitted or woven surgical meshes and vascular grafts, or braided sutures; and (3) flattened monofilaments for use as retraction tapes to hold and protect organs during surgical procedures.

An important aspect of the present invention deals with hybrid inorganic-organic monofilaments formed of $BaSO_4$ micro-/nanoparticles uniformly dispersed in an elastomeric absorbable matrix of a block copolymer of polyethylene glycol end-grafted with at least one cyclic monomer selected from the group represented by glycolide, a lactide, $\epsilon$-caprolactone, and trimethylene carbonate. More specifically, these monofilaments are designed to have the physicomechanical, chemical, and biological properties to allow their use as absorbable/disintegratable, load-bearing coils (or springs) in endoureteral devices, wherein the coils are covered with an absorbable knitted tubular mesh and both are coated with an absorbable binder coating. In turn, the endoureteral device can be used as an endoureteral stent which is capable of maintaining patency in a pathologically compromised ureter for at least one week; and degrades or disintegrates step-wise starting with the coating, the mesh, and then the coil. More specifically, at the conclusion of the stent functional period, the coil is expected to undergo catastrophic disintegration when the elastomeric organic matrix loses its mechanical integrity as it undergoes an advanced degree of hydrolytic degradation and becomes incapable of retaining the high density inorganic dispersed phase of $BaSO_4$ microparticles, which can easily be discharged by flowing urine without blocking the ureter.

This invention deals generally with an inorganic-organic hybrid melt-extruded filament having at least 10 weight percent of at least one type of inorganic micro-/nanoparticles dispersed in a thermoplastic organic polymeric matrix, wherein the inorganic micro-/nanoparticles are selected from the group represented by sulfates of di-, tri-, and tetravalent metals, phosphate salts, polymeric phosphate glasses, polymeric phosphate glass ceramics, phosphate ceramics, $ZrO_2$, and basic bismuth carbonate. Specifically, the inorganic components are selected from (1) sulfates of at least one of multivalent metal selected from the group Mg, Ca, Ba, Sr, Zr, Zn, Bi, and Fe; (2) phosphate salts selected from the group represented by $CaHPO_4$, $K_2HPO_4$, $KH_2PO_4$, $Na_2HPO_4$, $NaH_2PO_4$, $Ca_3(PO_4)_2$, $Ca_{10}(OH)_2(PO_4)_6$, and $Ca_2P_2O_7$; and/or (3) polymeric phosphate glasses which are derived from $P_2O_5$, CaO, and at least one oxide selected from the group represented by ZnO, SrO, $Na_2O$, $K_2O$, $SiO_2$, $Fe_2O_3$, and $ZrO_2$. The organic polymeric matrix of the inorganic-organic hybrid melt-extruded filament may consist of (1) a thermoplastic absorbable polyester having chain sequences derived from at least one cyclic monomer selected from the group represented by $\epsilon$-caprolactone, glycolide, a lactide, p-dioxanone, 1,5-dioxepan-2-one, trimethylene carbonate, and a morpholinedione; (2) an absorbable polyether-ester which may be derived from a polyethylene glycol end-grafted with at least one cyclic monomer selected from the group represented by $\epsilon$-caprolactone, glycolide, a lactide, trimethylene carbonate, p-dioxanone, 1,5-dioxepan-2-one, and a morpholinedione; or (3) polypropylene.

A specific aspect of this invention deals with an inorganic-organic hybrid melt-extruded filament having at least 10 weight percent of at least one type of inorganic micro-/nanoparticles dispersed in a thermoplastic organic polymeric matrix, wherein the filament is a monofilament having a diameter not exceeding 2 mm and the inorganic microparticles are $BaSO_4$ dispersed in an organic polymer which is an absorbable polyester having chain sequences derived from at least one cyclic monomer selected from the group represented by $\epsilon$-caprolactone, glycolide, a lactide, p-dioxanone, 1,5-dioxepan-2-one, trimethylene carbonate, and a morpholinedione, wherein the monofilament is heat-set into a coil for use as a component of an endoureteral stent.

Another specific aspect of this invention deals with an inorganic-organic hybrid melt-extruded filament having at least 10 weight percent of at least one type of inorganic micro-/nanoparticles dispersed in a thermoplastic organic polymeric matrix, wherein the filament is a monofilament having a diameter not exceeding 2 mm and the inorganic micro-/nanoparticles are $BaSO_4$ dispersed in an organic polymer which is an absorbable polyether-ester. Preferably, the absorbable polyether-ester is derived from a polyethylene glycol grafted with at least one cyclic monomer selected from the group represented by $\epsilon$-caprolactone, glycolide, a lactide, p-dioxane, 1,5-dioxepan-2-one, trimethylene carbonate and a morpholinedione. The monofilaments comprising the absorbable polyesters or the polyether-esters described above as the organic matrix can be used as (1) a component of an endourological stent, wherein the endourological stent is an endoureteral device comprising the hybrid monofilament as a coil covered with a knitted absorbable mesh and a binder surface coating; and/or (2) a radiopaque component of a medical device. Another specific aspect deals with an inorganic-organic hybrid melt-extruded filament comprising at least 10 weight percent of at least one type of inorganic micro-/nanoparticles dispersed in a thermoplastic organic polymeric matrix, wherein the aid filament can be used (1) as a radiopaque surgical device selected from the group represented by absorbable suture, absorbable stent, non-absorbable retraction tape, and non-absorbable suture; and/or (2) for cancer-related surgeries.

Thus, in accordance with the present invention the following general method for making hybrid, melt-extrudable compositions is employed. If needed, the particle size reduction of the inorganic component is achieved using cryogenic grinding at liquid nitrogen temperature or by jet-milling in a dry nitrogen atmosphere. The resulting micro-/nanoparticles are fractionated and sieved to remove all particles having a diameter exceeding 10μ. The sieved particles are dried at about 150° C. under a nitrogen atmosphere in the designated reactor for polymerization. The latter is designed to be used under dry nitrogen atmosphere or reduced pressure. The reactor also is equipped for mechanical stirring using a specially designed system for achieving extensive turbulent mixing and high shear at a broad range of viscosities. The polymer formation is then pursued under usual laboratory conditions with special attention given to (1) maintaining constant high shear stirring from the onset of the early monomer conversion until a high viscosity melt is attained—this is to insure uniform dispersion of the inorganic component in the polymerization charge; and (2) increasing the catalyst concentration to compensate for any catalyst adsorption or inactivation caused by the inorganic component. At the conclusion of the polymerization and attaining practically complete conversion, as determined by gel-permeation chromatography at the appropriate stages of the polymerization process, the polymeric composite is isolated, ground, and dried. The dried polymeric composite is purified by distilling traces of residual monomer under reduced pressure at elevated temperature. The composite is then characterized for its inorganic content (by extraction/mass balance), composition of extracted (using organic solvent extraction and then drying) polymer for molecular weight in terms of inherent viscosity, thermal analysis (be DSC) and composition (by IR and NMR).

Thereafter, the following general method of extruding the present inventive hybrid compositions into filaments is employed. The dry ground polymeric composition described above is extruded using a ¾" extruder equipped with a melt pump and a screen filter having a pore size of at least 45×45 μ. The temperatures at the different zones of the extruder are adjusted to insure continued melt flow at the required viscosity for attaining uniform extrudate take-up and cross-sectional adjustment. The solid extrudates are then oriented by drawing at one or two stage(s) using a set of heated and unheated Godeys. If so needed, the oriented extrudates are annealed at predetermined temperature and time under different pre-determined strain conditions.

Further illustrations of the present invention are provided by the following examples:

EXAMPLE 1

Synthesis of 20/80 by Weight BaSO$_4$/[40/60 by Weight (85/15 Molar ε-Caprolactone/Glycolide)/ι-Lactide Copolymer]

The reaction apparatus was comprised of a 1L stainless steel kettle with a 3-neck glass lid equipped with an overhead mechanical stirring unit, vacuum adapter, and nitrogen inlet. After obtaining a vacuum ≦0.5 mm Hg, the apparatus lowered into a high temperature oil bath that had been heated to 150° C. and the lid was flame dried. An initial charge of 100 grams barium sulfate was added to the kettle. (Note: BaSO$_4$ was sieved to remove any particles greater than 10 μ in size before using.)

The apparatus and its contents were placed under vacuum at 150° C. for 1.5 hour. The system was then purged with nitrogen. The temperature of the oil bath was decreased to 110° C. A second charge consisting of 135.6 grams (1.1899 moles) ε-caprolactone, 24.4 grams (0.210 moles) glycolide, 0.1165 grams (1.5332×10$^{-3}$ moles) propanediol, and 0.0756 grams (1.8664×10$^{34}$ moles) of stannous octanoate catalyst was added to the kettle while stirring. (Note: The second charge was dried in 40° C. vacuum oven for approximately 0.5 hours.) The temperature was increased to 180° C. After approximately 4.75 hours at 180° C., the temperature was decreased to 140° C. and the reaction was continued for an additional 16 hours. A third charge of 240 grams (1.6667 moles) ι-lactide was added to kettle while stirring. Once contents appeared to be completely and well mixed, a final charge of 53.4 milligrams (1.2×10$^{-4}$ moles) of stannous octanoate was added to kettle while stirring. The temperature was increased to 170° C. After 6 hours, the stirrer was stopped and the temperature was decreased to 160° C. The reaction was maintained at 160° C. for 16 hours.

The polymer was removed and ground using a 6 mm sieve. The ground material was sieved using a 1 mm sieve. Polymer was transferred to a 2L pear shaped glass flask and placed on a Buchi rotavapor. After obtaining a vacuum of 0.25 mm Hg, the flask was lowered into an oil bath. The temperature was increased to 40° C. After 2 hours at 40° C., the temperature of the oil bath was increased to 80° C. After 1 hour at 80° C., the temperature was increased to 110° C. Temperature was maintained at 110° C. for 4 hours.

The inherent viscosity using chloroform as a solvent was 1.30 dl/g. The molecular weight, $M_n$ and $M_w$, as determined by GPC using dichloromethane were 105 kDa and 180 kDa, respectively. The melting temperature and heat of fusion, as determined by differential scanning calorimetry, were 158.7° C. and 20.9 J/g, respectively.

EXAMPLE 2

Synthesis of 40/60 by Weight BaSO$_4$/[40/60 by Weight (75/25 Molar ε-Caprolactone/Glycolide)/ι-Lactide Copolymer]

The reaction apparatus was comprised of a 1L stainless steel kettle with a 3-neck glass lid equipped with an overhead mechanical stirring unit, vacuum adapter, and nitrogen inlet. After obtaining a vacuum ≦0.5 mm Hg, the apparatus was purged with nitrogen. An initial charge of 200 grams barium sulfate was added to the kettle. (Note: BaSO$_4$ was sieved to remove any particles greater than 10 μ in size before using.) The apparatus was then lowered into a high temperature oil bath that had been heated to 150° C.

The apparatus and its contents were placed under vacuum at 150° C. for 1.75 hour. The system was then purged with nitrogen. The temperature of the oil bath was decreased to 110° C. A second charge consisting of 89.6 grams (0.7860 moles) ε-caprolactone, 30.4 grams (0.262 moles) glycolide, 0.087 grams (1.15×10$^{-3}$ moles) propanediol, and 0.0566 grams (1.4×10$^{-4}$ moles) of stannous octanoate catalyst was added to the kettle. (Note: The second charge was dried in 40° C. vacuum oven for approximately 0.5 hours.) The temperature was increased to 180° C. After approximately 3 hours at 180° C., a second aliquot of 0.13 grams (3.16×10$^{-4}$ moles) stannous octanoate catalyst was added to the kettle while stirring. After an additional 2 hours at 180° C., the temperature was decreased to 140° C. and the reaction was continued for an additional 16 hours. A final charge consisting of 180 grams (1.25 moles) ι-lactide was added to kettle while stirring. Once contents appeared to be completely and well mixed, the temperature was increased to 170° C. After 5.5 hours, the temperature was decreased to 160° C. and the stirrer was stopped. The reaction was maintained at 160° C. for 17 hours.

The polymer was removed and ground using a 6 mm sieve. The ground material was sieved using a 1 mm sieve. Polymer was transferred to a 2L pear shaped glass flask and placed on a Buchi rotavapor. After obtaining a vacuum of 0.25 mm Hg, the flask was lowered into an oil bath. The temperature was increased to 40° C. After 2 hours at 40° C., the temperature of the oil bath was increased to 80° C. After 1 hour at 80° C., the temperature was increased to 110° C. Temperature was maintained at 110° C. for 4 hours.

The inherent viscosity using chloroform as a solvent was 1.05 dl/g. The molecular weight, $M_n$ and $M_w$, as determined by GPC using dichloromethane were 74 kDa and 132 kDa, respectively. The melting temperature and heat of fusion, as determined by differential scanning calorimetry, were 149.3° C. and 29.2 J/g, respectively.

EXAMPLE 3

Synthesis of 35/65 by Weight $BaSO_4$/(30/70 Molar ε-Caprolactone/Glycolide)

The reaction apparatus was comprised of a 1L stainless steel kettle with a 3-neck glass lid equipped with an overhead mechanical stirring unit, vacuum adapter, and nitrogen inlet. After obtaining a vacuum $\leq 0.5$ mm Hg, the apparatus was purged with nitrogen. An initial charge of 245 grams barium sulfate was added to the kettle. (Note: $BaSO_4$ was sieved to remove any particles greater than 10μ in size before using.), 132.1 grams (1.1592 moles) ε-caprolactone, 313.8 grams (2.7048 moles) glycolide, and 9.1 grams of a polyaxial polytrimethylene carbonate ($M_n$=3.2 kDa, made using trimethylene carbonate with trimethylolpropane and stannous octanoate as the initiator and catalyst, respectively) was added to the kettle. (Note: The charge was dried at 40° C. under vacuum for approximately 1 hour.) The system was then purged with nitrogen. The temperature was increased to 95° C. After approximately 1 hour at 95° C., an aliquot of 2.576 ml ($5.152 \times 10^{-4}$ moles) of a 0.2 M toluene solution of stannous octanoate was added to the kettle while stirring. The temperature was increased to 180° C. and stirred as long as possible. The reaction was maintained at 180° C. for 7 hours.

The polymer was removed and ground using a 6 mm sieve. The ground material was sieved using a 1 mm sieve. Polymer was transferred to a 2L pear shaped glass flask and placed on a Buchi rotavapor. After obtaining a vacuum of 0.25 mm Hg, the flask was lowered into an oil bath. The temperature was increased to 40° C. After 2 hours at 40° C., the temperature of the oil bath was increased to 80° C. After 1 hour at 80° C., the temperature was increased to 110° C. Temperature was maintained at 110° C. for 4 hours.

The inherent viscosity using HFIP as a solvent was 0.95 dl/g. The melting temperature and heat of fusion, as determined by differential scanning calorimetry, were 219.03° C. and 40.8 J/g, respectively.

EXAMPLE 4

Monofilament Fiber Extrusion of the Hybrid Composition of Example 1

A single screw extruder with four zones was used to extrude the polymer into monofilament. The polymer was extruded using a 0.6 mm die. A 325 line per inch filter pack was used. Zone 1 was maintained at 100° C.; Zone 2 was maintained at 152° C.; Zone 3 was maintained at 165° C.; and Zone 4/Spin Pack were maintained at 166° C. The metering pump was operated at 8 rpm while the take up roll was set at 40.5 rpm. The collected monofilament had diameters between 0.77 mm. The fiber was drawn at 4.6× in the first stage at 68° C., 1.2× in the second stage at 87° C., resulting in a diameter of 0.32 mm. The resulting fiber had a maximum load of 15.6 N, a strength of 28.2 kpsi, a modulus of 130 kpsi, and elongation of 90%. The free shrinkage was 20.4%. The fiber was annealed at 80° C. with 4% tension for 1 hour. The free shrinkage after annealing was 9.7%.

EXAMPLE 5

Monofilament Fiber Extrusion of the Hybrid Composition of Example 2

A single screw extruder with four zones was used to extrude the polymer into a monofilament. The polymer was extruded using a 0.6 mm die. A 325 line per inch filter pack was used. Zone 1 was maintained at 100° C.; Zone 2 was maintained at 150° C.; Zone 3 was maintained at 170° C.; and Zone 4/Spin Pack were maintained at 173° C. The metering pump was operated at 8 rpm while the take up roll was set between 35 and 40 rpm. The collected monofilament had diameters between 0.8 mm and 0.73 mm. The fiber was drawn at 4× in the first stage at 60° C., 3× in the second stage at 80° C., resulting in a diameter of 0.3 mm. The resulting fiber had a maximum load of 13.2 N, a strength of 28.6 kpsi, a modulus of 116 kpsi, and elongation of 67.5%. The free shrinkage was 66.6%. The fiber was annealed at 80° C. with 4% tension for 1 hour. Free shrinkage after annealing was 14.4%.

EXAMPLE 6

Monofilament Fiber Extrusion of the Hybrid Composition of Example 3

A single screw extruder with four zones was used to extrude the polymer into a monofilament. The polymer was extruded using a 0.6 mm die. A 325 line per inch filter pack was used. Zone 1 was maintained at 135° C.; Zone 2 was maintained at 210° C.; Zone 3 was maintained at 225° C.; and Zone 4/Spin Pack were maintained at 220° C. The metering pump was operated at 8 rpm while the take up roll was set between 55 and 65 rpm. The collected monofilament had diameters between 0.55 mm and 0.63 mm. The fiber was drawn at 4.5× in the first stage at 55° C., 0.5× in the second stage at 70° C., resulting in a diameter of 0.33 mm. The resulting fiber had a maximum load of 18.5 N, a modulus of 206 kpsi, and elongation of 29.6%.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. These subranges are also useful in carrying out the present invention.

What is claimed is:

1. An inorganic-organic hybrid melt-extruded filament comprising at least about 10 weight percent of at least one type of inorganic micro-/nanoparticles dispersed in a thermoplastic organic polymeric matrix, the matrix comprising an absorbable polyether-ester, the polyether-ester comprising a polyethylene glycol end-grafted with at least one cyclic monomer selected from the group consisting of ε-caprolactone, glycolide, a lactide, trimethylene carbonate, p-dioxanone, 1,5-dioxepan-2-one and a morpholinedione.

2. An inorganic-organic hybrid melt-extruded filament comprising at least about 10 weight percent of at least one type of inorganic micro-/nanoparticles dispersed in a thermoplastic organic polymeric matrix, the filament comprising a monofilament having a diameter of less than about 2 mm, the inorganic micro-/nanoparticles comprising $BaSO_4$ and the organic polymer matrix comprising an absorbable polyester comprising chain sequences derived from at least one cyclic monomer selected from the group consisting of ε-caprolactone, glycolide, a lactide, p-dioxanone, 1,5-dioxepan-2-one, trimethylene carbonate, and a morpholinedione, wherein the monofilament is heat-set into a coil for use as a component of an endoureteral stent.

3. An inorganic-organic hybrid melt-extruded filament comprising at least about 10 weight percent of at least one type of inorganic micro-/nanoparticles dispersed in a thermoplastic organic polymeric matrix, the filament comprising a monofilament having a diameter of less than about 2 mm, the inorganic micro-/nanoparticles comprising $BaSO_4$ and the organic polymer matrix comprising an absorbable polyether-ester.

4. An inorganic-organic hybrid melt-extruded filament as in claim 3 wherein the absorbable polyether-ester comprises a polyethylene glycol grafted with at least one cyclic monomer selected from the group consisting of ε-caprolactone, glycolide, a lactide, p-dioxane, 1,5-dioxepan-2-one, trimethylene carbonate and a morpholinedione.

5. An inorganic-organic hybrid melt-extruded filament as in claim 4 wherein the inorganic micro-/nanoparticles comprise $BaSO_4$.

6. An inorganic-organic hybrid melt-extruded filament as in claim 5 as a component of an endourological stent.

7. An inorganic-organic hybrid melt-extruded filament as in claim 6 wherein the endourological stent is an endoureteral device comprising the hybrid monofilament as a coil covered with a knitted absorbable mesh and a binder surface coating.

8. An inorganic-organic hybrid melt-extruded filament as in claim 7 for use as a radiopaque component of a medical device.

* * * * *